US006442536B1

United States Patent
Akhras et al.

(10) Patent No.: US 6,442,536 B1
(45) Date of Patent: Aug. 27, 2002

(54) METHOD FOR PREDICTING FLAMMABILITY LIMITS OF COMPLEX MIXTURES

(75) Inventors: Amer Wahid Akhras, Mahwah, NJ (US); Matthew Lincoln Wagner, Buffalo, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 09/487,385

(22) Filed: Jan. 18, 2000

(51) Int. Cl.[7] ............................. G06F 15/18; G06G 7/00
(52) U.S. Cl. ............................................ 706/21; 706/15
(58) Field of Search ....................................... 706/21, 15

(56) References Cited

U.S. PATENT DOCUMENTS 5,327,357 A  7/1994  Feinstein et al. ............ 700/271

OTHER PUBLICATIONS

T. Suzuki and M. Ishida, "Neural Network Techniques Applied to Predict Flammability Limits of Organic Compounds", *Fire and Materials*, vol. 19, 179–189 (1990).
T. Suzuki and K. Koide, "Short Communication: Correlation between Upper Flammability Limits and Thermochemical Properties of Organic Compounds", *Fire and Materials*, vol. 18, 393–397 (1994).
T. Suzuki, "Note: Empirical Relationship Between Lower Flammabilitiy Limits and Standard Enthalpies of Combustion of Organic Compounds", *Fir and Materials*, vol. 18, 333–336 (1994).
I. Wierzba, S.O. Bade Shrestha and G.A. Karim, "An Approach for Predictiing the Flammabilitiy Limits of Fuel/ Diluent Mixtures in Air", *Journal of the Institute of Energy*, Sep., 69, 122–130 (1996).
J.G. Hansel, J.W. Mitchell and H.C. Klotz, Predicting and Controlling Flammabilitiy of Multiple Fuel and Multiple Inert Mixtures, *Plant/Operations Progress*, vol. 11, No. 4, 213–217 (1992).
T.K. Subramanian and J.V. Cangelosi, "Predict Safe Oxygen in Combustible Gases", *Chemical Engineering*, Dec., 108–113 (1989).
W.H. Seaton, "Group Contribution Method for Predicting the Lower and Upper Flammable Limits of Vapors in Air", *Journal of Hazardous Materials*, 27, 169–185 (1991).

Primary Examiner—George B. Davis
(74) Attorney, Agent, or Firm—Bernard Lau

(57) ABSTRACT

This invention is directed to a method for predicting the flammability of complex mixtures using critical variables of structural groups comprising training data from the critical variables of each structural groups, the critical variables comprising compositional and thermochemical data from each of the structural groups to produce a neural network model; testing the trained data from the neural network model; and validating the trained and tested data from the neural network to accurately predict the flammability limit of an analogous complex mixture having similar structural groups.

12 Claims, 2 Drawing Sheets

METHOD FOR PREDICTING FLAMMABILITY LIMITS OF COMPLEX MIXTURES

FIELD OF THE INVENTION

This invention is generally related to predicting the flammability limits of chemical mixtures. More specifically, this invention relates to the use of neural networks as a model to predict the flammability limits of complex chemical mixtures.

BACKGROUND OF THE INVENTION

A vapor mixture containing combustible gaseous compounds ("fuels") and an oxidant (typically oxygen or oxygen containing gas) may be flammable if the mixture composition and conditions are such to sustain a flame upon ignition of the mixture. Often, such vapor mixture may contain an inert gas forming a tertiary system. The ignition of a flammable mixture results in propagation of a flame to the surrounding unburned fuel-oxidant-inert mixture, a rapid rise in pressure, and the potential for severe damage to equipment and/or injury or death to humans. Therefore, an understanding of the flammability characteristics of a ternary system containing a fuel(s), oxidant(s), and an inert(s) is essential to the prevention and/or mitigation of industrial explosions. In particular, the safe design, operation, and/or optimization of industrial process, which handle potentially flammable mixtures, rely on the knowledge of these flammability limits.

Figure 1:
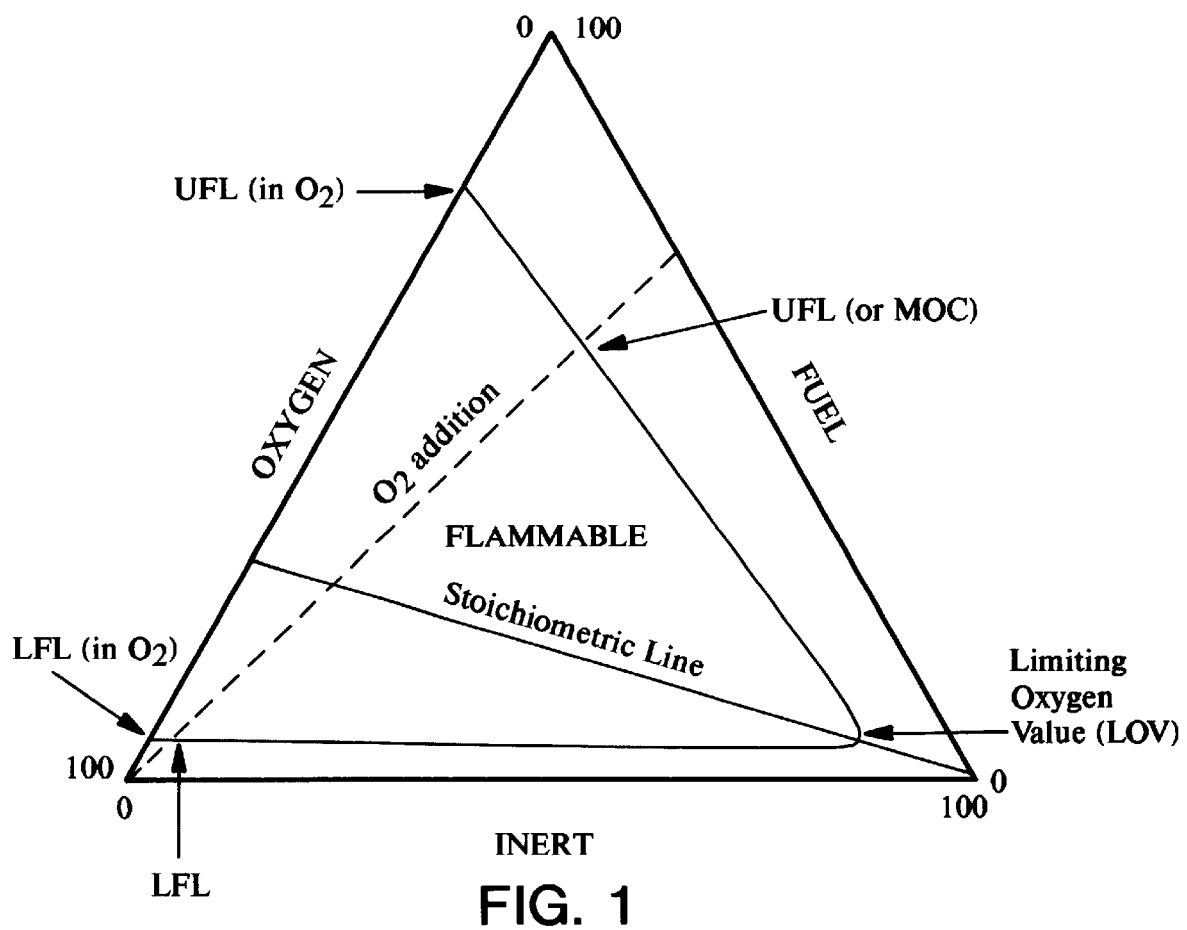

The composition of a mixture under a given set of conditions which are necessary to achieve a sustained flame define the flammability limit of a vapor mixture. Therefore, those factors, which influence reaction, heat, and mass transfer during combustion of the fuel-oxidant mixture, will impact the values of the flammability limits. Because a flammable mixture must contain a fuel and an oxidant, and may also contain an inert, defined as species which does not typically participate in the combustion reaction (i.e., $N_2$, Ar, He, $CO_2$, $H_2O$), the flammable envelope and its boundary (the flammability limits) are typically illustrated using ternary flammability diagrams. A typical ternary flammability diagram for a mixture containing a single fuel, a single oxidant, and an inert, at a given temperature and pressure is illustrated in FIG. 1. The flammable mixtures lie within the "flammability envelope", which is bounded above by the upper flammability limit (UFL), upper explosive limit (UEL), or the maximum oxygen concentration (MOC) and below by the lower flammability limit (LFL) or lower explosive limit (LEL). These two boundaries meet at a point referred to as the limiting oxygen value (LOV), the oxygen concentration below which no mixture of fuel, oxidant and inert is flammable.

Although the prior art addresses the measurement and prediction of flammability limits, it focused predominantly on simpler mixtures such as single fuels in air with single or two-component inert systems at or near normal temperature and pressure (25C and 1 atm). However, many industrial applications, including chemical processes, inerting, storage and transportation of flammable compounds, and many others, handle vapor mixtures containing an oxidant, oxygen, multiple inerts, and multiple fuels at elevated temperatures and pressure have not been believed to be addressed in the prior art. These mixtures will be referred to as "complex mixtures."

Typically, the measurement of flammability limits is then required to appropriately design safe systems and processes handling potentially flammable mixtures. However, the characterization of the flammability envelope of a complex mixture through experimental tests can be quite difficult, time consuming, and expensive. An ability to predict the flammability limits of complex mixtures would serve as a very valuable tool to numerous industries. Such a tool would also help when exploring novel processes and process conditions. With a better understanding of the mixture flammability properties, one can pinpoint the conditions of interest, thereby minimizing the time and cost associated with extensive flammability measurements.

However, to develop a predictive model from first principles is a very formidable task. Neural networks, however, can offer a means of modeling these complex, non-linear relationships without detailed knowledge of the fundamental relationships, including thermodynamics, kinetics, heat, and mass transfer, which dictate the flammability behavior of these complex mixtures. This invention describes a novel approach for predicting the flammability limits of complex mixtures using neural networks.

An abundance of flammability limit data and techniques for predicting flammability limits exists in the prior art. A review of the prior art does reveal a number of predictive models which attempt to address the issue of predicting flammability limits. The authors of the relevant prior art have taken a number of approaches, including Le Chatelier's principle, constant adiabatic flame temperature (CAFT), linear and non-linear regression, group contribution techniques, and neural networks to tackle this problem.

Le Chatelier's principle is a traditional and simple approach used often to predicts LFL and UFL's of fuel mixtures in air based on the flammability limits of each fuel and the fuel mixture composition. Another approach is based on the observation that lower paraffins exhibit constant adiabatic flame temperatures at the limits of flammability. A number of empirical and semi-empirical models for predicting the flammability limits, temperature effects, pressure effects also exist in the prior art. Although neural networks have been used extensively to model the non-linear relationships which exist between a certain set of inputs and outputs, neural network based techniques for predicting flammability limits is limited.

For purposes of this invention, Flammability limits shall mean the point in which a flame initiated from an adequate ignition just fails to propagate throughout the fuel/oxidant mixture.

There is believed to be no teaching in the prior art for using neural networks based techniques to predict the upper and lower flammability limits of complex mixtures. It is, therefore, desirable in the art to provide for a method of predicting the flammability limits of complex mixtures.

SUMMARY OF THE INVENTION

This application is directed to a method for predicting the flammability limits of a complex mixture using critical variables of structural groups comprising the steps of training data from the critical variables of each structural groups, the critical variables comprising compositional and thermochemical data from each of the structural groups to produce a neural network model; testing the trained data from the neural network model; and validating the trained and tested data from the neural network to accurately predict the flammability limit of an analogous complex mixture having similar structural groups.

DETAILED DESCRIPTION OF THE PREFERRED EMBODIMENT

The method for predicting flammability limits which is disclosed in this invention is believed to be more robust than any other technique available in the prior art in its attempt to handle complex mixtures containing multiple fuels, multiple inert species (i.e., He, Ar, $CO_2$, N2, $H_2O$) at varying temperatures and pressures.

Figure 2:
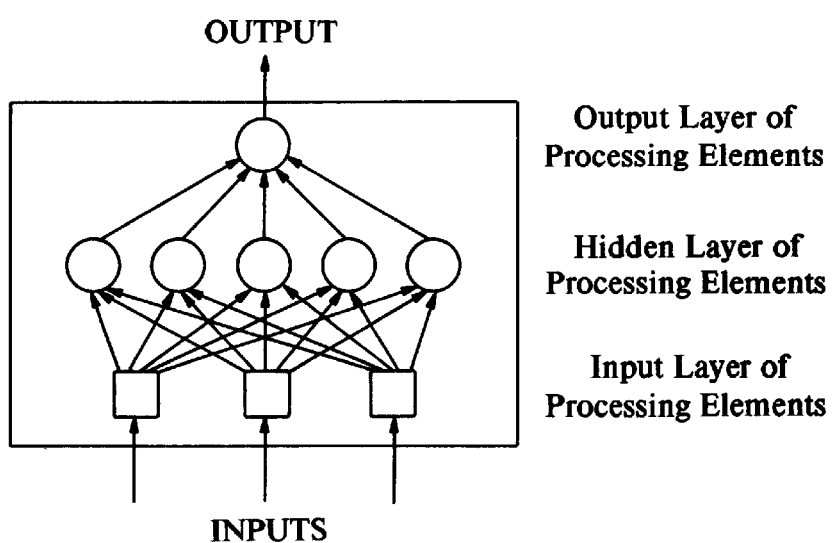

An artificial neural network is an interconnection of simple processing elements, units, or nodes whose functionality is loosely based on that of biological neurons. Each processing element transforms the summation of several weighted inputs ("synapse") into an output using non-linear transfer functions (such as sigmoid functions). As a result, neural networks are also described as parallel distributive processors. The structure of these interconnected processing elements can vary, but one of the most widely used architectures is the Multiple Layer Perceptron (see FIG. 2) consisting of an input layer, a layer of hidden processing elements, and an output layer.

By using an iterative process or "learning" technique, the values of input weights and transfer function parameters for each given processing element are adjusted until a certain objective function, which is based on how well the model predicts the output, is satisfied. Back propagation is the most common technique for adjusting the weights of the inputs. The key to effective training of a neural network to capture the general trends in the data requires data. However, when training neural networks, one must always be careful not to over-specify or over fit the data in order to ensure generalization of the network. To this end, the data upon which it is trained is typically divided into a training set and a test set. The model is built by continuously adjusting weights and adding processing elements until its performance has reached a minimum criteria for both the training and data sets. Because the test data set is not completely independent of the training process, a small portion of the available data is set aside and used to test the model's performance. The objective is to build a model, which performs well for all three data sets, thereby preventing overfitting and ensuring a generalized model. Therefore, the effectiveness of a neural network relies on data to train the network to recognize the general relationships between the inputs and the output(s).

A variety of learning algorithms, including adaptive gradient learning and the Kalman learning rule, are used to train neural networks. Numerous guidelines and algorithms have also been developed for the transformation of input data into a form more suitable for training of a neural network, variable selection, determination of the optimum number of hidden processing elements, and specification of the size and composition of training, validation, and test sets. Therefore, the construction of a neural network model involves data selection, data transformation, variable selection, neural network building, network training, and evaluation. Because a neural network is a sophisticated non-linear regression technique with a limited basis in the process fundamentals, the network is most effective when handling inputs which are well-represented within the training data input space. However, knowledge of the process or application is critical to the optimum selection of training data, transformation of data, and evaluation of model performance.

As a result, neural networks work well in the categorization, modeling, and classification of data for which there is no known mathematical function or fundamental understanding of the relationship between the inputs or independent variables and the output(s). Neural network applications are abundant and diverse and have included investment analysis, signature analysis, process control (i.e., optimization and control of a steel making process), and marketing.

For the application of neural networks to the prediction of complex mixture flammability limits, an extensive amount of flammability data (totaling about 4300 points for about 70 chemical compounds) has been gathered from the literature to serve as training data.

Flammability Model Description

The first step in building a neural network based model for predicting the flammability limits of complex mixtures was to define the network inputs and outputs. In this case, the single network output, the predicted variable, was the upper flammability limit, the lower flammability limit, or the limiting oxygen value. The variables that were believed to have played an important role in determining the flammability characteristics of a vapor mixture, including but not limited to temperature, pressure, the extent of inerting, mixture compositions, component physical and thermodynamic properties, were represented by these network inputs. The objective was then to capture the relationships between these critical variables and the flammability properties, specifically the flammability limits, of complex mixtures while still creating a robust model which can handle complex mixtures at varying temperature and pressure based only on compositional and thermochemical data. To this end, the vapor mixture was divided into three components: 1) the inert, containing all the inert species; 2) the fuel, containing all flammable compounds, generally hydrocarbons; and 3) an oxidant, typically oxygen. The inert and fuel components of the mixture are then characterized by a set of variables, which capture the effect of each component on the flammability limits of the mixture.

For simplification, the inert was treated as a diluent which affected the thermal properties of the mixture, acting as both a heat sink and medium for heat transfer during combustion and flame propagation. Therefore, one first defined the total inert to total fuel molar ratio (I/F) as a network input to capture the extent of inerting:

$$\frac{I}{F} = \frac{\sum_{i=1}^{N_I} y_i^I}{\sum_{i+1}^{N_F} y_i^F}$$

where $y_i^I$ is the mole fraction of inert species i in the mixture of fuel and inert only, $y_i^F$ the mole fraction of the fuel species i in the mixture of fuel and inert only, $N_I$ the total number of inert species, and $N_F$, the total number of fuel species.

The inert component was then defined in terms of its thermal properties, including the molar heat capacity and the thermal conductivity in an attempt to capture the thermal effect of the inerts on the flammability properties of the mixture. In order to ensure generalization of the model for all inerts, the inert species in the mixtures were lumped into a single inert defined in terms of the inert mixture's molar heat capacity ($C_P^I$) and thermal conductivity ($k^I$), which are calculated using common summation formulas and the inert component compositions:

$$C_P^I = \sum_{i=1}^{N_i} X_i^I C_{P,i}^I$$

$$k^I = \sum_{i+1}^{N_O} X_i^I k_i$$

$N_I$=the total number of inerts within the inert component;
$X_i^I$=the mole fraction of inert species I within the inert mixture; $C_{P,i}^I$=the standard molar heat capacity of inert species I; and $k_i$=the thermal conductivity of inert species I.

Other physical properties of the inert component, which impacted the flammability of the mixture, was also be used as the basis of additional network inputs. These may include density and viscosity.

A similar approach was used to characterize the thermochemical effect of the reactive fuel compounds in the mixture. In this example, the heat of combustion in addition to the heat capacity of the fuel mixture (calculated using a similar summation formula) were as input variables:

$$\Delta H_c = \sum_{i=1}^{N_F} X_i^F \Delta H_c^i$$

$$C_P^F = \sum_{i=1}^{N_F} X_i^F C_{P,i}^F$$

where, $\Delta H_c$=the mixture molar heat of combustion; $\Delta H_c^i$= the pure component heat of combustion of fuel species I; $C_P^F$=the fuel mixture molar heat capacity; and $C_{p,i}^F$=the pure component molar heat capacity of fuel species I.

A group contribution approach was then used to reconcile the kinetics and thermodynamics during combustion of the fuels while again creating a simple yet robust model. Group contribution methods were used for estimating hydrocarbon thermodynamic and physical properties based only on knowledge of the compound's chemical structure.

First order structural groups (second order groups account for nearest neighbor effects) and additional inputs accounting for non-hydrocarbon fuels, such as CO, $NH_3$, HCN, and $H_2$, were defined as input variables for the neural network. The database of flammability limit data, which was later used for building and training of the neural network, represented 70 different chemical compounds. 37 structural groups (shown in Table 1) were required to describe each of these compounds. These groups were then used to lump the multi-component fuel mixture into a single fuel defined on the basis of chemical structure. The following equation was used:

$$G_m^F = \frac{\sum_{i=1}^{N_F} X_i^F G_m^i}{\sum_{m=1}^{N_{SG}} \sum_{i=1}^{N_F} X_i^F G_m^i}$$

where, $G_m^i$=the contribution of structural group m (of which there are 34) in fuel i of $N_F$ fuels in the fuel mixture; $X_i^F$=the mole fraction of fuel i in the fuel mixture; $N_{SG}$=the total number of structural groups (34, in this example); and $G_m^F$=the normalized contribution of structural group m in the lumped fuel.

Figure 3:
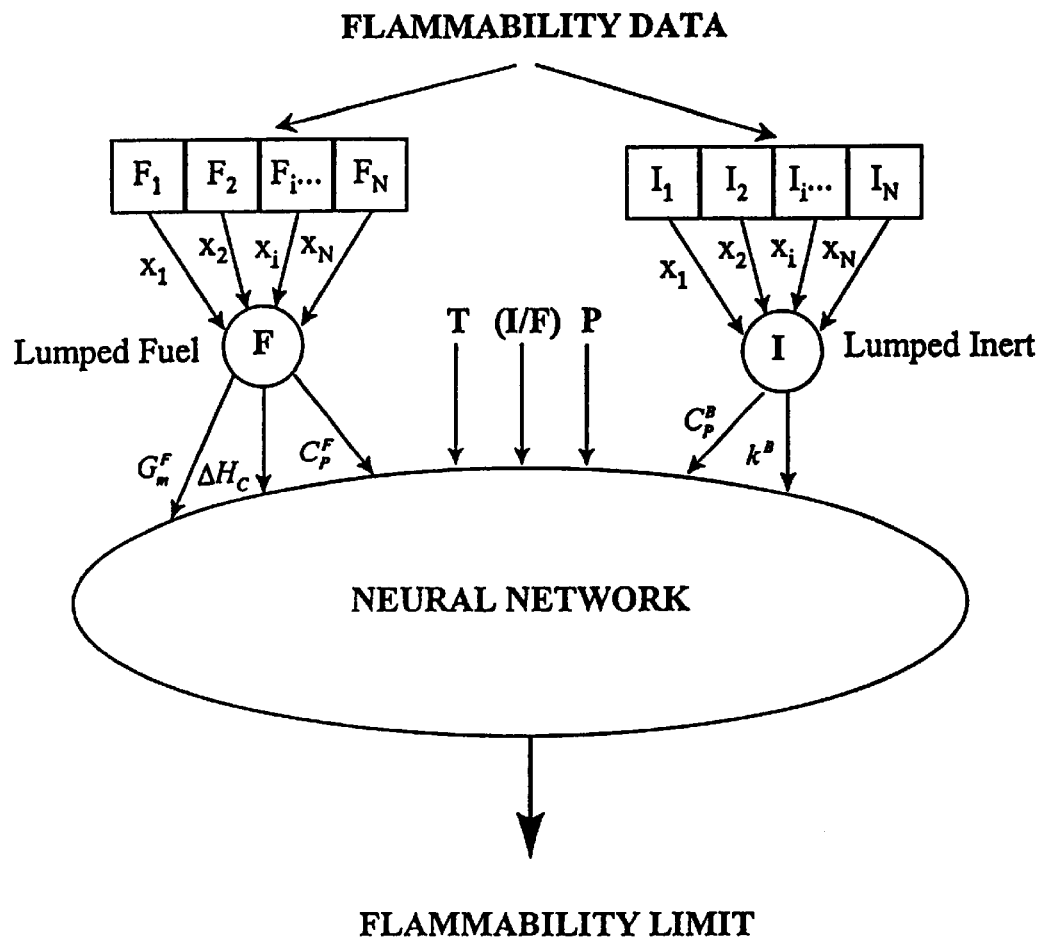

Therefore, in this example, these structural groups, the overall heat capacities of the fuel mixture, the overall heat capacity and thermal conductivity of the inert mixture, and the heat of combustion of the fuel mixture account for all of the inputs to the neural network. This approach for specifying the inputs to the neural network enabled simplification and generalization of the model for predicting the flammability limits of vapor mixtures containing multi-component fuels and ballast gases at varying temperatures and pressures. This approach for specifying the inputs to the neural network is illustrated in FIG. 3.

TABLE 1

Structural Groups Used in Neural Network Model $G_m^i$
$CH_4$
—$CH_3$
—$CH_2$
—CH
—C
$H_2C$=
HC≡
≡C≡
HCArom
—CArom
O=CH
O=C
O=C—O—
—$NH_2$
—NH
N
=N—
—N=0
—$NO_2$
—C≡N
—OH
—O—
—S—
—SH
—S=O
—Cl
—Br
$CH_2$(Ring)
CH(Ring)
C(Ring)
—O—(Ring)

Example of Model Performance When Predicting the Maximum Oxygen Concentration (MOC) or Upper Flammability Limit (UFL) of a Gaseous Mixture of Fuel, Inert, and Oxygen The next step was to build and train the neural network on flammability data. In this example, the objective was to predict the UFL or MOC of fuel-inert-oxidant mixtures based only on knowledge of composition, chemical structure, and thermochemical data. A preliminary analysis was performed to model the upper flammability limit or the maximum oxygen concentration (MOC). Approximately 4300 data points collected from the literature, representing 70 different chemical compounds, served as the basis of the neural network building and training process. All of the data was transformed into the designated set of inputs and outputs and used for training and testing of the neural network. Based on recommended training, testing, and validation data set rules, approximately 20% of the data was set aside as an independent validation set, while 70–80% of the remaining data was used to train the neural network and the rest for testing of the network. This was done to ensure generalization of the model and prevent overfitting of the data.

Figure 4:
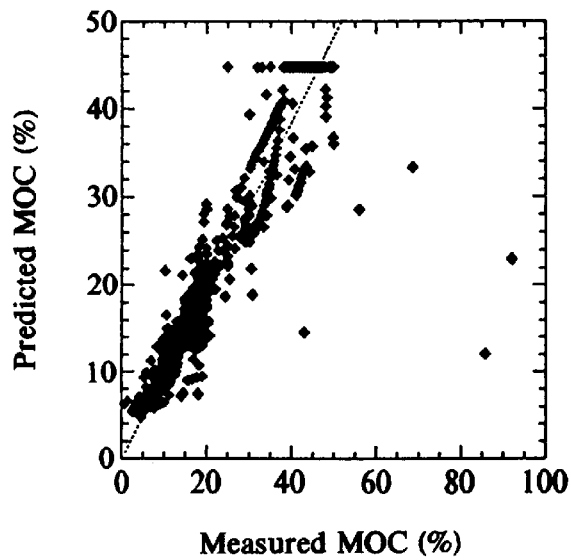

In this example, a cascaded neural network consisting of 129 transformed inputs, 9 hidden processing elements and a single output provided the best results. Table 2 summarizes the correlation coefficient (R) and accuracy (percentage of predictions that fall within 5% of the corresponding measurement) of the model for the four data sets: training data, test data, validation data, and all of the data. The MOC's predicted by the neural network are plotted against the measured MOC for the entire data set in FIG. 4. Good correlation between prediction and the data for all four data sets demonstrates that the model has done a good job in capturing the general relationships between the input variables and the output while avoiding overfitting of the data. There are some outlying predictions, which deviate significantly from the measured values. This is expected due to limitations in the scope of the available data and variability in flammability measurements. When using a neural network, even distribution of the data across the defined input space is critical to the performance of the model. As more complex mixture data becomes available to use as training data, the model will continue to learn and improve.

TABLE 2

Results of Neural Network Model Performance

| Data Set | Correlation Coefficient (R) | Accuracy (5%) |
| --- | --- | --- |
| All | 0.939 | 94.2 |
| Training | 0.950 | 94.9 |
| Test | 0.904 | 92.8 |
| Validation | 0.944 | 93.3 |

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A method for predicting the flammability limits of a complex mixture using critical variables of structural groups comprising a. training data from said critical variables of each structural groups, said critical variables comprising compositional and thermochemical data from each of said structural groups to produce a neural network model;
   b. testing said trained data from said neural network model; and
   c. validating said trained and tested data from said neural network to accurately predict the flammability limit of an analogous complex mixture having similar structural groups.

2. The method of claim 1 wherein said treating step comprises treating an inert component as a diluent to affect the thermal properties of said complex mixture.

3. The method of claim 2 wherein said treating step comprises training as a critical variable the total inert to total fuel molar ratio having the formula:

$$\frac{I}{F} = \frac{\sum_{i=1}^{N_I} y_i^I}{\sum_{i+1}^{N_F} y_i^F} G_m^i$$

where $y_i^I$ is the mole fraction of inert species i in the mixture of fuel and inert only; $y_i^F$ is the mole fraction of the fuel species i in the mixture of fuel and inert only; $N_I$ the total number of inert species; and $N_F$, the total number of fuel species.

4. The method of claim 1 wherein said complex mixture comprises an input critical variable for the inert component having a heat capacity ($C_P^I$) calculated using the formula:

$$C_P^I = \sum_{i=1}^{N_I} X_i^I C_{P,i}^I$$

where $N_I$ is the total number of inerts within the inert component; $X_i^I$ is the mole fraction of inert species I within the inert mixture; $C^{P,iI}$ is the standard molar heat capacity of inert species I; and $k_i$ is the thermal conductivity of inert species I.

5. The method of claim 1 wherein said complex mixture comprises an input critical variable for the inert component having a thermal conductivity ($k^I$) calculated using the formula:

$$k^I = \sum_{i+1}^{N_O} X_i^I k_i$$

where $N_I$ is the total number of inerts within the inert component; $X_i^I$ is the mole fraction of inert species I within the inert mixture; $C_{P,i}^I$ is the standard molar heat capacity of inert species I; $k_i$ is the thermal conductivity of inert species I.

6. The method of claim 1 wherein said complex mixture comprises an input critical variable for the inert component having a molar heat of combustion ($\Delta H_c$) calculated using the formula:

$$\Delta H_c = \sum_{i=1}^{N_F} X_i^F \Delta H_c^i$$

where $\Delta H_c^i$ is the pure component heat of combustion of fuel species I.

7. The method of claim 1 wherein said complex mixture comprises an input critical variable for the reactor fuel mixture having a fuel mixture molar heat capacity $C_P^F$ using the formula:

$$C_P^F = \sum_{i=1}^{N_F} X_i^F C_{P,i}^F$$

where $C_{P,i}^F$ is the pure component molar heat capacity of fuel species I.

8. The method of claim 1 wherein said complex mixture comprises a first order structural groups and additional inputs accounting for non-hydrocarbon fuels, such that a normalized contribution of said structural group m ($G_m^i$) uses the formula:

$$G_m^F = \frac{\sum_{i=1}^{N_F} X_i^F G_m^i}{\sum_{m=1}^{N_{SG}} \sum_{i=1}^{N_F} X_i^F G_m^i}$$

where $G_m^i$ is the contribution of structural group m (of which there are 34) in fuel i of $N_F$ fuels in the fuel mixture; $X_i^F$ is the mole fraction of fuel i in the fuel mixture; $N_{SG}$ is the total number of structural groups (34, in this example); and $G_m^F$ is the normalized contribution of structural group m in the lumped fuel.

9. The method of claim 1 where said complex mixtures comprise a plurality of reactive fuels and inert species.

10. The method of claim 1 wherein said validating steps produce a single network output.

11. The method of claim 1 wherein said critical variables are selected from the group consisting of temperature, pressure, extent of inerting, mixture composition, component physical properties, density and viscosity.

12. The method of claim 1 wherein said structural groups are selected from the group consisting of $CH_4$, $-CH_3$, $-CH_2$, $-CH$, $-C$, $H_2C=$, $HC=$, $=C=$, HCArom, $-$CArom, $O=CH$, $O=C$, $O=C-O-$, $-NH_2$, $-NH$, $N$, $=N-$, $-N=O$, $-NO_2$, $-C=N$, $-OH$, $-O-$, $-S-$, $-SH$, $-SH$, $-S=O$, $-Cl$, $-Br$, $CH_2$(Ring), CH(Ring), C(Ring), $-O-$(Ring).

* * * * *